United States Patent [19] [11] Patent Number: 4,735,619
Sperry et al. [45] Date of Patent: Apr. 5, 1988

[54] SYRINGE AND SYRINGE ACTUATOR

[76] Inventors: Charles R. Sperry, 19 Crawford Rd., Westport, Conn. 06880; Paul J. Bladyka, R.R. 2, Box 651, Chester, Vt. 05143

[21] Appl. No.: 417,440

[22] Filed: Sep. 13, 1982

[51] Int. Cl.⁴ ............................................. A61M 5/00
[52] U.S. Cl. .................................. 604/208; 604/246; 604/218
[58] Field of Search ................... 604/44, 131, 57, 159, 604/164, 169, 170, 183, 189, 207, 208, 211, 228, 218, 246, DIG. 12, DIG. 13; 73/3; 222/1, 49

[56] References Cited

U.S. PATENT DOCUMENTS

| | | | |
|---|---|---|---|
| 2,170,599 | 8/1939 | Stricklen | 604/218 |
| 2,530,909 | 11/1950 | Riggs | 73/425.6 |
| 3,306,502 | 2/1967 | Harris, Jr. | 604/218 |
| 3,317,083 | 5/1967 | Morrill | 222/1 |
| 3,606,086 | 9/1971 | Drummond et al. | 222/49 |
| 3,774,605 | 11/1973 | Jewett | |
| 3,828,987 | 8/1974 | Drummond et al. | 604/208 X |
| 3,835,854 | 9/1974 | Jewett | |
| 3,838,688 | 10/1974 | May et al. | |
| 3,877,287 | 4/1975 | Duntz, Jr. | 73/3 |
| 3,923,060 | 12/1975 | Ellinwood, Jr. | |
| 4,150,672 | 4/1982 | Whitney et al. | |
| 4,360,019 | 11/1982 | Portner et al. | |

Primary Examiner—Stephen C. Pellegrino
Attorney, Agent, or Firm—St.Onge Steward Johnston & Reens

[57] ABSTRACT

An elongate flexible syringe for the injection of fluids is formed with an elongate flexible tube and an elongate flexible rod sized to move through the bore of the tube to control the discharge of liquid in the tube. A cartridge is provided to store the flexible rod in a coiled form. The flexible rod is advanced by a syringe actuator having a control housing to which the cartridge is conveniently mounted. The actuator includes a mechanism for energizing the flexible rod and cause it to advance in a precisely controlled manner. A device for detecting motion or the absence of motion of the flexible rod is described so that the proper operation and emptying of the tube can be continually monitored. The elongate flexible syringe is particularly convenient to be carried by a person for the timed regulated injection of medicine such as insulin.

20 Claims, 2 Drawing Sheets

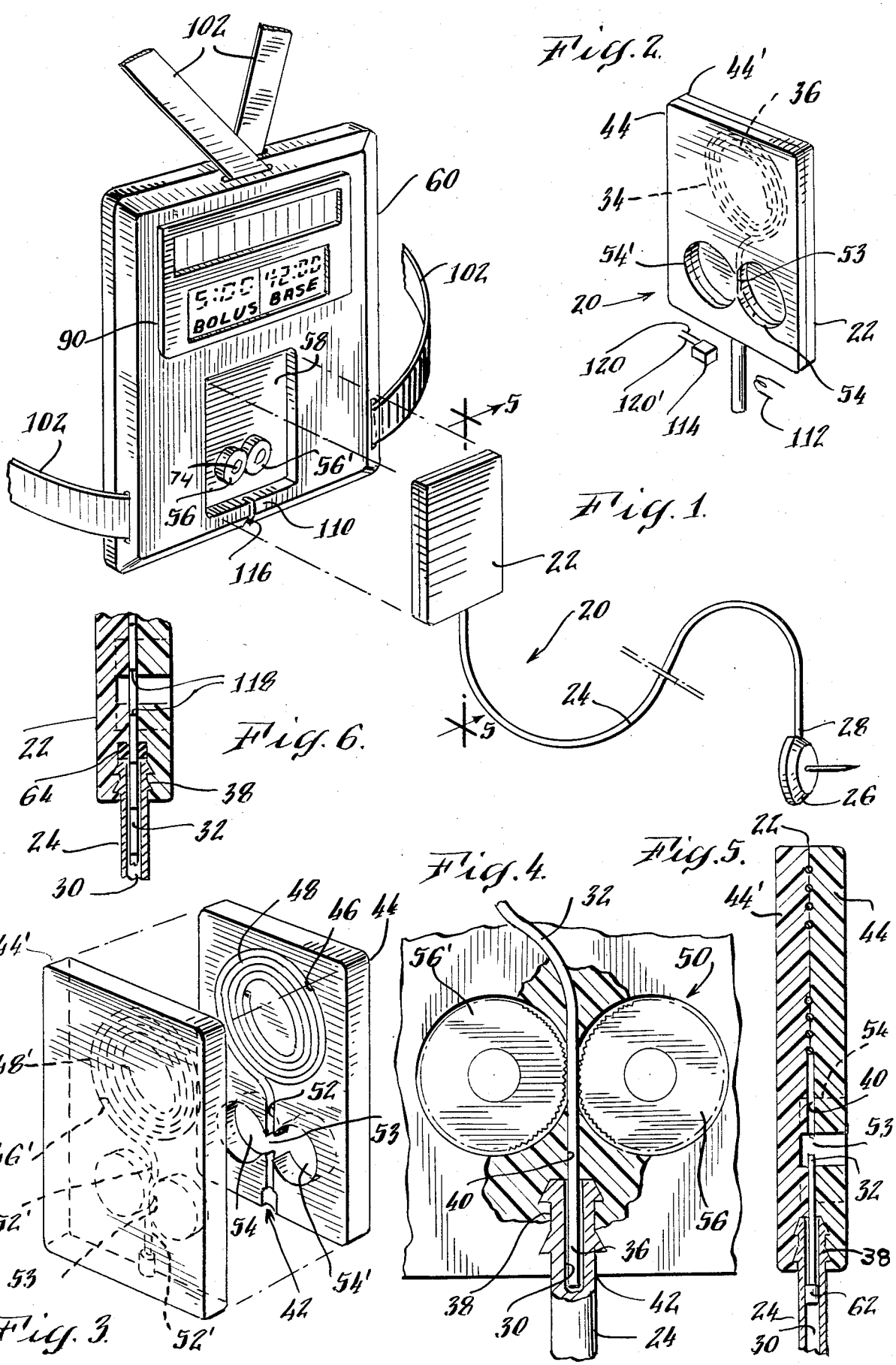

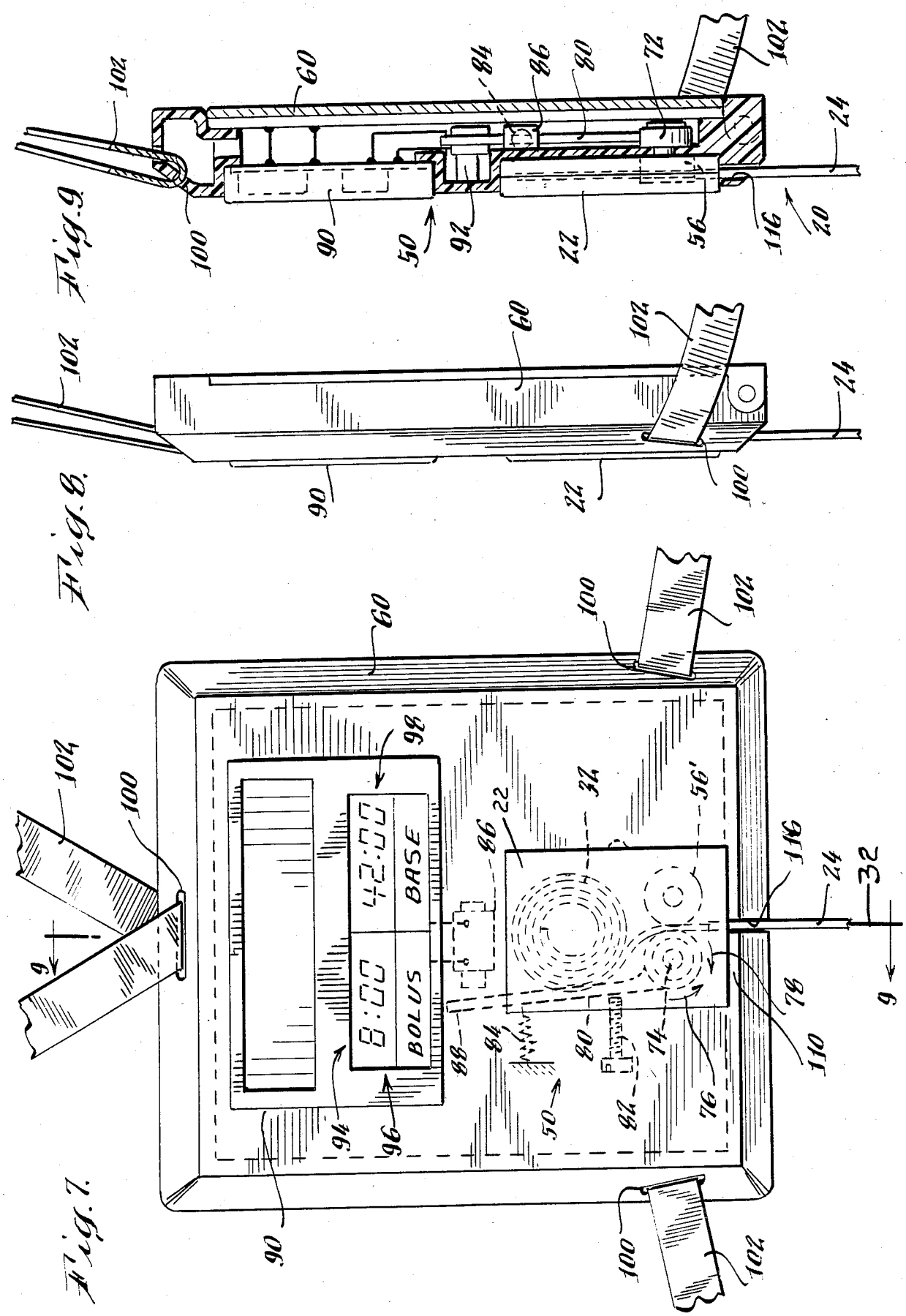

SYRINGE AND SYRINGE ACTUATOR

FIELD OF THE INVENTION

This invention generally relates to a syringe and more specifically to a syringe for the controlled injection of fluids into a body and adapted to be worn by the person being injected.

BACKGROUND OF THE INVENTION

Devices for the controlled infusion of fluids into bodies are known in the art, see for example U.S. Pat. Nos. 4,150,672 to Whitney et al or 3,923,060 to Ellenwood. The '672 patent teaches a fluid injection apparatus to be worn by the person while the '060 patent describes an implantable device to dispense a medication.

Devices are available to dispense insulin into a person on a timed basis that is expected to correspond with the need by the individual for the medication. Problems with various known techniques for injecting a fluid into a body is their complexity, lack of adaptability to the physical movements of the person and the need to provide conveniently installed replacements as the fluid supply is depleted on the currently installed device.

SUMMARY OF THE INVENTION

A syringe in accordance with the invention may be conveniently installed in a small housing worn by the person to be injected and is easily applied to different places on the body. This is obtained with an elongate flexble syringe formed of an elongate flexible tube having a bore filled with the liquid to be dispensed. An elongate flexible rod is located inside the elongate flexible tube and, as the rod is advanced, fluid is dispensed from the distal end of the tube.

With a syringe in accordance with the invention a compact syringe actuator device may be provided that is easily worn at one convenient place while an injection point of the fluid from the syringe may be at a different location through tubing that serves to store the liquid. Little loss by way of unused fluid occurs.

A syringe in accordance with the invention can be in the form of a small cartridge that is inserted in a housing that contains a drive and a suitable control to provide a controlled advance of the flexible rod through the tube. A precisely timed release or injection of the fluid can be obtained commensurate with the needs of the patient.

The precision of the dispensation of liquid from a syringe in accordance with the invention is obtained with a flexible rod whose insertion into the bore of the flexible tube may be precisely controlled. By virtue of the long length of the bore of the flexible tube and the small crossectional dimension of the rod, small doses of liquid can be dispensed in an accurate and repeatable manner.

With a syringe in accordance with the invention, the discharge of liquid can be conveniently monitored and the amount of liquid that is dispensed measured. This may be done by providing the elongate flexible rod with indicia whose passage is sensed with an optical detector located in the housing to which the syringe is connected.

It is, therefore, an object of the invention to provide a syringe that is particularly suitable for controlled timed discharge of a fluid for use by an ambulatory patient, and which is convenient to install with a prefilled dosage while discharging the fluid in a precisely controllable manner. It is a further object of the invention to provide a fluid dispenser which enables the dispensation of very small quantities of fluid from a supply with little loss of unused fluid.

These and other objects of the invention can be understood from the following description of a syringe in accordance with the invention and described with reference to the drawings.

BRIEF DESCRIPTION OF DRAWINGS

FIG. 1 is a partially exploded perspective view of a syringe and actuator housing in accordance with the invention;

FIG. 2 is a perspective view of a cartridge housing employed with a syringe in accordance with the invention;

FIG. 3 is an exploded view of the cartridge housing as shown in FIG. 2;

FIG. 4 is an enlarged view of a syringe drive employed in the housing of FIG. 7;

FIG. 5 is a enlarged side section view of the syringe taken along lines 5—5 in FIG. 1

FIG. 6 is an enlarged side section view of a portion of a syringe in accordance with the invention;

FIG. 7 is an enlarged front view of a syringe drive housing and syringe in accordance with the invention;

FIG. 8 is a side view of the syringe drive housing shown in FIG. 7; and

FIG. 9 is a section view of the syringe drive housing taken along the line 9—9 in FIG. 7.

DETAILED DESCRIPTION OF DRAWINGS

With reference to FIGS. 1 through 6, a syringe 20 is shown formed of a cartridge housing 22 and an elongate flexible tube 24. A hypodermic needle 26 is connected to the distal end 28 of the tube 24 to enable direct injection of fluid stored in a bore 30 of tube 24. The syringe 20 is normally sterilized and supplied in a sterile package (not shown).

The cartridge housing 22 contains an elongate flexible rod 32 that is used to pass into the bore 30 of flexible tube 24 to discharge fluid from the distal end 28 and needle 26. Flexible rod 32 is stored in cartridge housing 22 in a coiled form in a recess 34 with a distal end 36 inserted into a proximal end 38 of flexible tube 24. The rod 32 is threaded through a passageway 40 that communicates with recess 34 and terminates at an exit port 42.

Flexible rod 32 may be formed of a variety of materials. One material found suitable is a nylon monofilament which has a crossection selected to fit into and move through bore 30 of flexible tube 24. Other materials may be selected such as a flexible metal wire that is a straight smooth wire or a tightly coiled wire. The flexible rod 32 should have sufficient rigidity to be moved through an elongate bore 30 of tube 24 without buckling, yet preferably not be so rigid as to excessively rigidize the syringe as the rod 32 is advanced into the bore 30. Preferably rod 32 should be made of a material that may be stored in recess 34 as a coil 36 as shown in FIG. 2 with the coil 36 being unwound as the flexible rod 32 is advanced into bore 30 of flexible tube 24.

The elongate flexible tube 24 may be formed of a material that preferably does not have a high friction contact with flexible rod 32. A material such as nylon or polytetrafluorethylene or other flexible tube material that is compatible with the fluid in the bore 30 of the tube 24 may be used. One form of tube 24 may be a flexible catheter material whose lumen is used to store the fluid. Preferably the wall of the tube 24 is sufficiently strong to withstand pinching and avoid kinking as the syringe 20 is worn by a patient.

The length of flexible tube 24 is selected commensurate with the amount of fluid to be stored. A flexible tube 24 of the order of about 12 inches (30 cm) in length may be used to store a milliliter occupying a volume of a cubic centimeter, of liquid with a diameter for bore 30 of several millimeters. In such case a flexible rod 32 of a slightly smaller diameter is employed to discharge the liquid from the tube 30.

The cartridge housing 22 is formed of two mating segments 44, 44', each of which include part of a rod storing recess 34 with complementary shaped recesses 46, 46'. The latter recesses have spirally shaped grooves 48, 48'. The recesses 46, 46' and grooves 48, 48' face each other in an assembled cartridge housing 22 in such manner that a flexible rod 32 is retained in a spiral form by a spirally shaped conduit formed by the grooves 48, 48'. When a rod 32 is stored inside housing 22 it may be freely slidingly removed by a side engaging syringe actuating mechanism 50.

The flexible rod storing recess 34 communicates through guideway 46 with an exit port 48 where the proximal end 38 of flexible tube 24 is affixed to the housing 22. The end 38 of tube 24 may be affixed to housing 22 with cement or a frictional fit or in such other manner as is convenient and suitable. Guideway 40 is formed with two separate grooves 52, 52' each in a housing segment 44. The grooves 52, 52' intersect at 53 with portions of circular recesses 54, 54' in each housing segment 44 so that the flexible rod 32, when threaded through guideway 40 and port 42 into tube 24, at least partially passes through recesses 54, 54'. In this manner the juxtaposed drive wheel 56 and idler 56' of the flexible rod actuating drive mechanism 50 may be precisely operatively engaged with flexible rod 32 by simply snap fitting cartridge housing 22 into a mating recess 58 of a control housing 60.

When the syringe 20 is operatively mounted to control housing 60, wheel 56 and idler 56' frictionally each engage a side of the flexible rod 32. This may be obtained by mounting wheel 56 and idler 56' with slight lateral resilience sufficient to be normally urged towards each other and thus slightly spread apart to accommodate rod 32 when the cartridge 22 is mounted to control housing 60.

Operation of flexible rod 32 to dispense fluid from tube 24 may be with a piston element 62 located in and pushed through bore 30 of tube 24 of rod 32 as shown in FIG. 5. Another dispensing technique involves displacement of liquid by advancing flexible rod 32 into bore 30 through a seal 64 affixed to the proximal end 38 of tube 24 as shown in FIG. 6.

The syringe actuator drive mechanism 50 advances flexible rod 32 into flexible tube 24 with small motions initiated by a motor ratchet type actuator as illustrated in the view of FIGS. 7 and 9. The actuator includes a one-way rotary drive 72, such as a sprague drive, which is mounted to shaft 74 in common with drive wheel 56. The drive 72 freely rotates about shaft 74 in the direction of arrow 76 but causes a rotation of shaft 74 when rotated in the direction of arrow 78. A lever 80 that is affixed to drive 72 is urged towards an adjustable stop 82 by a spring 84. A solenoid 86 is positioned opposite end 88 of lever 80 to attract and thus pivot lever 80 in the direction of arrow 78, thereby causing a corresponding advance of the flexible rod 32 into tube 24. The actuation of solenoid 86 is obtained with timed pulses that occur at intervals corresponding to the desired dosage of the medicine in the syringe 20. The amount of motion imparted by lever 80 on rod 32 and thus the amount of the dosage is controlled by adjusting stop 82.

Housing 60 includes a suitable control circuit 90 powered by a battery 92. Circuit 90 includes a timer and, if desired, a display 94 to indicate at 96 the amount being dispensed as well as such other information at 98 applicable to the medicine in syringe 20. The timer in circuit 90 may be a solid state circuit with selectable settings not shown, and delivers sufficiently powerful drive pulses to actuate solenoid 86. Control housing 60 is adapted to be conveniently worn by a patient and includes suitable strap retainers 100 so that straps 102 may affix the housing to a desired place on the patient's body.

With a syringe 20 and control housing 60 in accordance with the invention, a dosage of medicine can be conveniently and yet accurately applied on a continual basis. For example, a syringe 20 may include a supply of insulin that is conveniently injected into the patient at a desirable place. This may be at a location that is remote from the control housing, yet without a wasting of medicine through the use of a long supply tube. An accurate repeatable dosage may be given to the patient by accurately regulating the advance of the flexible rod 32.

One advantage of a syringe in accordance with the invention resides in the ability to monitor the operation and thus assure the continued periodic injection of medicine. This may be obtained by employing at 110 in control housing 60 an LED light source 112 and light sensor 114 that are operative across a slot 116 in which tube 24 of syringe 20 is held. The source 112 and sensor 114 are schematically shown in FIG. 2. When tube 24 and rod 32 are transparent and flexible rod 32 is provided with regularly spaced reflective or opaque indicia or bands 118 as shown in FIG. 6 so that the passage and thus the motion of rod 32 can be detected by monitoring the output signal present on lines 120, 120' from sensor 114. Such monitoring function can be obtained with circuit 90 which would mate the changes in the signal level on lines 120; 120' in a given time period. In this manner an audible alarm may be generated from a projector inside control housing 60 whenever the flexible rod 32 fails to move.

Having thus described a syringe and control housing in accordance with the invention, its advantages can be appreciated. Variations from the described embodiment may be made without departing from the scope of the invention.

What is claimed is:

1. A syringe comprising:
   an elongate flexible liquid supply tube having a bore to store a liquid; and
   an elongate flexible rod sized to slidingly fit without buckling into the bore of the tube and having a length selected to cause ejection of liquid stored in the bore of the tube as the rod is advanced into the bore.

2. The syringe as claimed in claim 1 and further including:
   means for storing the elongate flexible rod, said flexible rod being stored in said means in a coiled form.

3. The syringe as claimed in claim 1 wherein said rod is formed of an extruded filament.

4. The syringe as claimed in claim 3 wherein the flexible rod is formed of a plastic filament.

5. The syringe as claimed in claim 1 wherein the tube is formed of an elongated flexible catheter having a lumen, and wherein the flexible rod is sized to fit through the lumen.

6. The syringe as claimed in claim 1 wherein the ratio of the length of the flexible rod to a crossectional dimension of the bore of the tube is greater than about fifty.

7. The syringe as claimed in claim 1 and further comprising:
    means for sealing the bore between the flexible rod and the tube at a front end thereof where the rod enters the bore of the tube; and
    wherein the elongate flexible rod is so sized in crossection relative to that of the bore as to cause said ejection of liquid by displacement thereof by the rod as it is advanced into the bore of the tube.

8. The syringe as claimed in claim 1 and further comprising a piston element sized to fit inside the tube bore and move therealong, said piston element slidingly and sealingly engaging the tube.

9. The syringe as claimed in claim 1 wherein the flexible rod is provided with optically detectable regularly spaced indicia.

10. The syringe as claimed in claim 9 and further including:
    means for detecting said indicia and generating a signal indicative thereof.

11. The syringe as claimed in claims 1, 2, 3, 4, 5, 6, 7, 8 or 9 and further including:
    actuator means for engaging the elongate flexible rod to move the rod through the bore of the elongate flexible tube.

12. The syringe as claimed in claim 11 wherein said actuator means further includes:
    an idler element and a drive wheel, said idler element and drive wheel being justaposed on opposite sides of the flexible rod to cooperatively grip the rod between them; and
    means for automatically rotating the drive wheel in precisely repeatable incremental steps to move the rod through the bore of the tube.

13. The syringe as claimed in claim 12 wherein said means for rotating the drive wheel includes ratchet means for actuating the drive wheel in one direction, a solenoid, and means for operatively coupling the solenoid to the ratchet means.

14. The syringe as claimed in claim 1, 2, 3, 4, 5, 6, 7, 8 or 9 and further incluidng:
    a cartridge housing adapted to affix to a rod advancing control housing, said cartridge housing having a recess retaining a coiled shape of the flexible rod, an exit port and a guideway extending from the recess to the exit port, the guideway being sized to freely enclose and guide the flexible rod from the recess to the exit port; and
    means for affixing the elongate flexible tube to the cartridge housing in alignment with the exit port.

15. The syringe as claimed in claim 14 wherein said cartridge housing recess is provided with a spiral groove sized to retain the flexible rod in a coiled form while enabling the rod to be drawn out of the spiral groove for insertion in the bore of said tube.

16. The syringe as claimed in claim 14 wherien the cartridge housing is further provided with:
    a drive wheel receiving recess that at least partially intersects the guideway to enable operative engagement with the flexible rod at said intersection to cause movement of the flexible rod.

17. The syringe as claimed in claim 16 wherein the cartridge housing is further provided with an idler receiving recess that at least partially intersects the guideway opposite to the drive wheel receiving recess.

18. The syringe as claimed in claim 17 and further including:
    a control housing having a syringe actuator which includes a drive wheel and an idler element located to respectively freely fit into the drive wheel receiving recess and idler receiving recess when the cartridge housing is affixed to the control housing; and
    means in the control housing for rotating the drive wheel to move the rod through the tube.

19. The syringe as claimed in claim 1, 2, 3, 4, 5, 6, 7, 8 or 9 and further incluidng:
    means for generating a signal representative of a motion of the flexible rod relative to the tube.

20. The syringe as claimed in claim 19 wherein the motion signal generating means includes a light source and light sensor respectively operatively positioned to detect the presence of the flexible rod.

* * * * *